United States Patent [19]

Godfroid et al.

[11] Patent Number: 5,017,588

[45] Date of Patent: May 21, 1991

[54] 5-(ω-AMMONIO ACYLOXY METHYLENE) TETRAHYDROFURANS AND TETRAHYDROTHIOPHENES AND A THERAPEUTIC COMPOSITION CONTAINING SAME

[75] Inventors: Jean-Jacques Godfroid, Paris; Pierre Braquet, Garches; Francoise Heymans, Paris, all of France

[73] Assignee: Societe De Conseils De Recherches Et D'Applications Scientifiques, France

[21] Appl. No.: 485,448

[22] Filed: Feb. 27, 1990

Related U.S. Application Data

[63] Continuation-in-part of Ser. No. 199,948, May 27, 1988, abandoned.

[30] Foreign Application Priority Data

May 29, 1987 [GB] United Kingdom ............... 8712693

[51] Int. Cl.$^5$ ............... C07D 405/12; C07D 409/12; A61K 31/44
[52] U.S. Cl. ............... 514/336; 546/283; 546/284
[58] Field of Search ............... 546/283, 284; 514/336

[56] References Cited

PUBLICATIONS

Chemical Abstracts, vol. 110 (No. 21) abst. No. 192,663-c; May 22, 1989.
Chemical Abstracts, vol. 110 (No. 25) abst. No. 231,446f Jun. 19, 1989.

*Primary Examiner*—Alan L. Rotman
*Attorney, Agent, or Firm*—Lucas & Just

[57] ABSTRACT

This invention relates to new tetrahydrofurans and tetrahydrothiophenes of the general formula

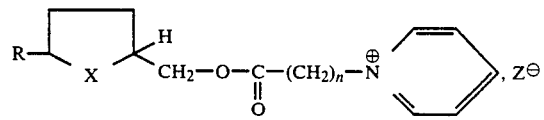

wherein X stands for O or S, $\eta$ is an integer from 1 to 6, R stands for various hydrocarbon substituents and $Z^{\ominus}$ is a pharmaceutically acceptable anion, to a preparation process of said compounds and to therapeutic compositions of matter containing the same.

2 Claims, No Drawings

5-(ω-AMMONIO ACYLOXY METHYLENE) TETRAHYDROFURANS AND TETRAHYDROTHIOPHENES AND A THERAPEUTIC COMPOSITION CONTAINING SAME

This application is a continuation-in-part of application Ser. No. 199,948 filed May 27, 1988, now abandoned.

The present invention relates to new 5-(ω-ammonio acyloxy methylene) tetrahydrofurans and tetrahydrothiophenes of the general formula:

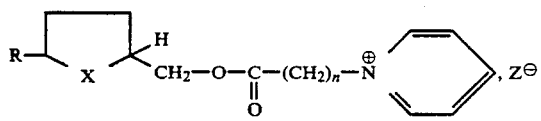

wherein
X stands for O or S;
n is an integer from 1 to 6;
R stands for a straight or branched $C_1$–$C_{13}$ alkyl, a $C_5$–$C_{10}$ cycloalkyl, an optionally substituted phenyl or an optionally substituted phenyl alkyl with 1 to 5 carbon atoms in the alkyl moiety, the substitutions $R_1$ to $R_5$ of the phenyl ring, of formula:

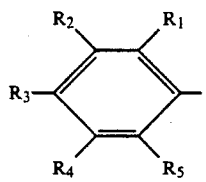

being $CH_3$ or $OCH_3$ and $Z^\ominus$ is a pharmaceutically acceptable anion.

The invention relates to these compounds under the form of each of their possible stereoisomers or of any mixture of the same.

These compounds are more particularly interesting as anti PAF agents (P A F means platelets aggregation factor) with the corresponding activity as anti-anaphylactic, antithrombotic, anti-ischemic, immunodepressors and acting also against immune alteration of kidney, against various shocks, against skin allergies and intestinal ulcers induced by endotoxine for instance.

The compounds according to the invention may be prepared by reacting a compound of formula I:

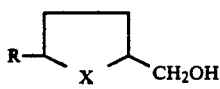

with a compound of formula II:

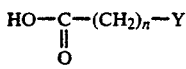

wherein X, n and R are as defined above and Y is an halogen.

The reaction is suitably carried out in an inert solvent such as dry $CHCl_3$ at room temperature in the presence of triisopropylbenzenesulfonylchloride and pyridine and lead to the intermediate formula III:

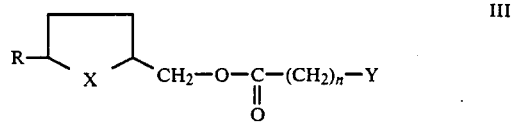

wherein X, n, R and Y are as defined above; this compound is further treated by pyridine for the obtention of the title compounds.

The compound of formula I may be synthesized according to the following steps:

An intermediate triol is prepared in accordance with the following steps:

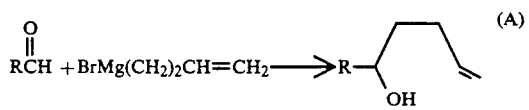

This reaction is carried out under standard Grignard reaction conditions. The Grignard reagent is suitably prepared in situ by using dry magnesium turnings in dry ether and adding the brominated butene thereto. The substituted formaldehyde is added to the Grignard reagent. The substituted formaldehyde may be added by a stream of nitrogen gas into the solution of the Grignard reagent. The reaction is stopped by the addition of ice and dilute sulfuric acid, thus making the intermediate compound (A).

(A) is reacted with benzyl chloride (BzCl) to form the compound (B).

(B) is oxidized by cold dilute potassium permanganate ($KMnO_4$) to form (C), the triol intermediate:

The triol (C) can be cyclized into a tetrahydrofuran or tetrahydrothiophene ring using protecting groups, mesylation and treatment either by water or $Na_2S$, the different synthesis methods depending on whether R is aromatic or aliphatic, and whether X is oxygen or sulfur.

(1) When R is aromatic and X=O, (C) is cyclized by hydrogenation with $H_2/Pd$ under standard acidic conditions, forming the substituted tetrahydrofuran (D) of formula I:

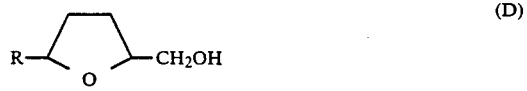

where R is aromatic.

(2) When R is aliphatic and X=O, the compound of formula I is made as follows:

(C) from above is hydrogenated with $H_2/Pd$. Here, cyclization is prevented by performing the hydrogenation under basic conditions such as by adding calcium carbonate ($CaCO_3$), forming the triol:

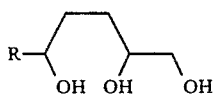

The primary hydroxyl is substituted with the protecting group triphenylmethyl chloride (Tr) [$(C_6H_5)_3CCl$] and the other hydroxyl groups are substituted with mesyl chloride (MS) ($CH_3SO_2Cl$) to form the compound (E):

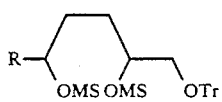

(E) is then cyclized in water and hexametapol (HMPT) to form the following compound:

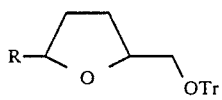

which is hydrogenated with $H_2/Pd$ to form the substituted tetrahydrofuran (F) where R is aliphatic:

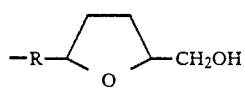

(3) To form the compound of formula I where X=S and R is aliphatic or aromatic, the foregoing steps up to compound (E) are followed. The sulfur is introduced into the ring by the addition of $Na_2S$ in HMPT to form the compound:

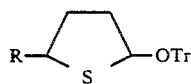

The triphenylmethyl chloride is removed by adding formic acid to form the substituted tetrahydrothiophene (G):

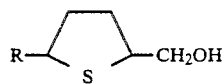

where R may be aliphatic or aromatic.

(D), (F) and (G) as described above are all variants of the substituted tetrahydrofurans and tetrahydrothiophenes of formula I used as the starting materials in the present invention.

The invention will be better understood from the following examples.

EXAMPLE 1

2-tridecyl 5-(5-pyridinio pentanoyloxymethylene) tetrahydrofuran chloride

X=O, n=4, R=$CH_3(CH_2)_{12}$, $Z^\ominus = Cl^\ominus$

Step a: Preparation of 2-tridecyl 5-(5-chloropentanoyloxymethylene) tetrahydrofuran. III A=$(CH_2)_4$, X=Cl.

A mixture of 2 g (7 mmoles) of 2-tridecyl tetrahydrofuryl 5-methanol, 1.43 g (10.5 mmoles) of 5-chloro pentanoic acid and 4.24 g (14 mmoles) of triisopropylbenzene sulfonyl chloride in dry $CHCl_3$ (20 ml)/pyridine (10) was stirred at room temperature for 24 hours.

The reaction was quenched by adding 50 ml $H_2O$ then alkalinised ($Na_2CO_3$) and the aqueous layer reextracted with $CHCl_3$. After washing successively with $H_2O$, $H_2SO_4$ 1N, $H_2O$, $Na_2CO_3$ and $H_2O$, the organic layer was dried ($MgSO_4$) and concentrated in vacuo. The residue was then chromatographied on a silica gel column using 5 to 10% ether in petroleum ether to yield 1.42 g of the title compound as an oil.

IR (film) 2950, 2880 (C—H), 1750 (C=O), 1190, 1110 (C—O) cm$^{-1}$. $^1$HNMR (80 MHz, $CDCl_3$, HMDS), $\gamma$4.02 (m, 4 H, $CH_2OCO+CH—O$), 3.55 (t, 2H, $CH_2Cl$), 2.35 (t, 2H, $CH_2CO$), 2.22-1.37 (m, 10H, $CH_2—C—O$, $CH_2—C—CO+CH_2—C—Cl$), 1.22 (large s, 22H, $(CH_2)_{11}$), 0.81 (t, 3H, $CH_3$).

Step b: Preparation of 2-tridecyl 5-(5-pyridinio pentanoyloxymethylene) tetrahydrofuran chloride.

0.5 g (1.24 mmoles) of the compound prepared in step (a) were refluxed overnight in 5 ml dry pyridine. After concentration in vacuo, the brown residue was purified on a silica gel column using successively 1, 2, 5 and 10% MeOH in $CHCl_3$ leading to 0.4 g of the title compound as a hygroscopic waxy compound.

IR (film) 3060 (aromatic C—H), 2860, 2950 (C—H), 1740 C=O), 1640 (C=N), 1590 (C=C), 1180, 1100 (C—O) cm$^{-1}$. $^1$HNMR (80 MHz, $CDCl_3$, HMDS) $\gamma$9.71 (d, 2H, CH=N), 8.65

(t, 1H, 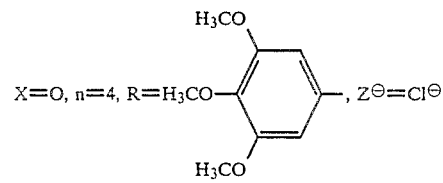 H), 8.25 (t, 2H, 2 CH=C—N), 5.12 (t, 2H, $CH_2N$), 3.97 (m, 4H, $CH_2—OCO+2CH—O$), 2.42 (t, 2H, $CH_2CO$), 2.27-1.42 (m, 10H, $CH_2—C—O$, $CH_2—C—CO+CH_2—C—N$), 1.22 (large s, 22H, $(CH_2)_{11}$), 0.82 (t, 3H, $CH_3$).

EXAMPLE 2

2-(3,4,5-trimethoxyphenyl) 5-(5-pyridinio pentanoyloxymethylene) tetrahydrofuran chloride X=O, n=4, R=(3,4,5-trimethoxyphenyl), $Z^\ominus = Cl^\ominus$ Analogous to example 1 (a) (b) starting from 2-(3,4,5 trimethoxyphenyl) tetrahydrofuryl-5 methanol to obtain the title compound as a very hygroscopic compound.

IR (KBR) 3060 (aromatic, C—H) 2920 (C—H), 1735 (C=O), 1635 (C=N), 1595 (C=C), 1180, 1130, 1035

(C—O) cm$^{-1}$. $^1$HNMR (80 MHz, CDCl$_3$, HMDS) γ:9.71 (d, 2H, CH=N), 8.48

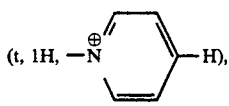

8.08 (t, 2H, CH=C—N), 6.62 (s, 2H, aromatic H), 5.52-4.77 (m, 3H, CH$_2$N+φ—CH—O), 4.42 (m, 1H, CH—O), 4.17 (t, 2H, CH$_2$OCO), 3.87 (s, 9H, CH$_3$O), 2.63-1.55 (m, 10H, CH$_2$CO+CH$_2$—C—CO+CH$_2$—C—N+CH$_2$—C—O).

EXAMPLE 3

2-(2,4,6-trimethylphenyl) 5-(5-pyridiniopentanoyloxymethylene) tetrahydrofuran chloride

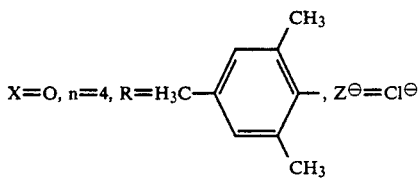

Analogous to example 1 (a) (b) starting from 2-(2,4,6-trimethylphenyl) tetrahydrofuryl-5-methanol to obtain the title compound as a very hygroscopic compound.

$^1$HNMR (80 MHz, CDCl$_3$, HMDS) γ9.28 (d, 2H, CH=N), 8.42 (m, 1H,

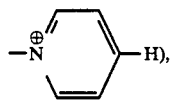

7.98 (m, 2H, CH=C—N), 6.75 (s, 2H, aromatic H), 5.25 (m, 1H, φ—CH—O), 4.90 (m, 2H, CH$_2$N), 4.60-3.96 (m, 3H, CH$_2$OCO+CH—O), 2.57-1.37 (m, 10H, CH$_2$—CO+CH$_2$—C—O+CH$_2$—C—N), 2.27 (s, 6H, ortho—CH$_3$), 2.17 (s, 3H, para—CH$_3$).

EXAMPLE 4

2-tridecyl 5-(5-pyridiniopentanoyloxymethylene) tetrahydrothiophene chloride

Analogous to example 1 (a) (b) starting from 2-tridecyl tetrahydrothienyl-5-methanol to obtain the title compound as a highly hygroscopic compound.

$^1$HNMR (80 MHz, CDCl$_3$, HMDS) γ9.35 (d, 2H, CH=N), 8.56 (t, 1H,

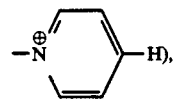

8.15 (m, 2H, CH=C—N), 4.97 (m, 2H, CH$_2$N), 3.45 (m, 2H, CH—S), 2.37 (t, 2H, CH$_2$CO), 2.22-1.4 (m, 12H, CH$_2$—C—N+CH$_2$—C—CO+CH$_2$—C—S), 1.2 (large s, 22H, (CH$_2$)$_{11}$), 0.82 (t, 3H, CH$_3$).

TOXICOLOGY

The compounds of the invention have been administered to mice for determination of acute LD$_{50}$. For all the compounds of the invention LD$_{50}$ was over 300 mg/Kg (IP or SC) and 600 mg/Kg (PO).

PHARMACOLOGY

A proof of the pharmaceutical interest of the compounds of the invention has been established by the following pharmaceutical experimentation.

Inhibition of the platelets aggregation on New Zealand rabbits.

The experimentation was conducted on platelets with plasma of New Zealand rabbits. Blood samples were taken from auricular artery and placed in a citrate buffer (3.8%; pH 7.4); blood was further centrifugated for 15 mn at 1200 RPM. The tested sample was prepared in DMSO, then poured on platelets rich plasma for 1 mn, then a dose of 2.5 nM of PAF was added. The determination is made on a Cronolog Coultronics apparatus which determines the transmission percentage corresponding to the maximum height of the peak before the desaggregation. The percentage of variation of the inhibition with respect to the transmission percentage is calculated (control:pure DMSO). This method was described in detail in LABORATORY INVESTIGATIONS, Vol. 41, No. 3, p. 275, 1979, JEAN-PIERRE CAZENAVE, Dr. MED., JACQUES BENVENISTE, Dr. MED., AND J. FRASER MUSTARD, M. D., "Aggregation of Rabbits Platelets by Platelet-Activating Factor is independent of the Release Reaction and the Arachidonate Pathway and inhibited by Membrane-Active Drugs".

The results demonstrate that the compounds inhibit the aggregation induced by 2.5 nM of PAF. Five tests made on 5 different rabbits allowed us to calculate the IC$_{50}$ of the various compounds using the linear regression test.

The values for IC$_{50}$ on platelets have been found as follows:

Example 1: 3.04 0.10$^{-6}$
Example 2: 3.7 0.10$^{-5}$
Example 3: 3.86 0.10$^{-6}$
Example 4: 1.7 0.10$^{-5}$.

We claim:
1. A tetrahydrofuran or tetrahydrothiophene of the formula

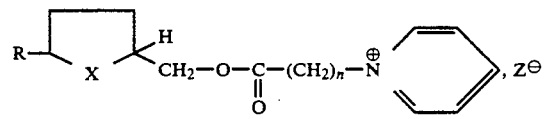

wherein
X stands for O of S;
n is an integer from 1 to 6;
R stands for a straight or branched C$_1$-C$_{13}$ alkyl, a C$_5$-C$_{10}$ cycloalkyl, a phenyl or a substituted phenyl having the formula:

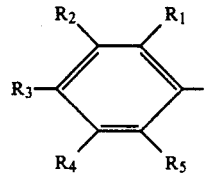

R$_1$ to R$_5$ is H, CH$_3$ or OCH$_3$ and Z$^⊖$ is a pharmaceutically acceptable anion.

2. A therapeutic composition of matter, comprising as an essential ingredient therein an effective amount of a compound according to claim 1 in admixture with the appropriate diluent or carrier.

* * * * *

UNITED STATES PATENT AND TRADEMARK OFFICE
CERTIFICATE OF CORRECTION

PATENT NO. : 5,017,588
DATED : May 21, 1991
INVENTOR(S) : Jean-Jacques Godfroid et al.

It is certified that error appears in the above-identified patent and that said Letters Patent is hereby corrected as shown below:

Abstract, line 5, change "$\eta$" to --n--.

Column 3, line 35, change $-R-\underset{O}{\langle\phantom{x}\rangle}-CH_2OH$ to $R-\underset{O}{\langle\phantom{x}\rangle}-CH_2OH$ Column 4, line 22, change "$\gamma$" to --$\delta$--.

Column 4, line 37, change "$\gamma$" to --$\delta$--; and change "CH=N" to --CH=$\overset{\oplus}{N}$--.

Column 4, line 45, change "CH=C-N" to --CH=C-$\overset{\oplus}{N}$--; and change "CH$_2$N" to --CH$_2\overset{\oplus}{N}$--.

Column 5, line 2, change "$\gamma$" to --$\delta$--; and change "CH=N" to --CH=$\overset{\oplus}{N}$--.

Column 5, line 9, change "CH=C-N" to --CH=C-$\overset{\oplus}{N}$--.

Column 5, line 29, change "$\gamma$" to --$\delta$--.

Column 5, line 30, change "CH=N" to --CH=$\overset{\oplus}{N}$--.

Column 5, line 37, change "CH=C-N" to --CH=C-$\overset{\oplus}{N}$--.

UNITED STATES PATENT AND TRADEMARK OFFICE
CERTIFICATE OF CORRECTION

PATENT NO. : 5,017,588

DATED : May 21, 1991

INVENTOR(S) : Jean-Jacques Godfroid et al.

It is certified that error appears in the above-identified patent and that said Letters Patent is hereby corrected as shown below:

Column 5, line 38, change "$CH_2N$" to --$CH_2\overset{\oplus}{N}$--.

Column 5, line 51, change "$\gamma$" to --$\delta$--.

Column 5, line 52, change "$CH=N$" to --$CH=\overset{\oplus}{N}$--.

Column 5, line 59, change "$CH=C-N$" to --$CH=C-\overset{\oplus}{N}$--; and change "$CH_2N$" to --$CH_2\overset{\oplus}{N}$--.

Column 5, line 61, change "$CH_2-C-N+CH_2-C-CO+CH_2-C-S$" to --$CH_2-C-\overset{\oplus}{N}+CH_2-C-CO+CH_2-C-S$--.

Column 6, line 18, change "desaggreagation" to --desaggregation--.

Column 6, line 49, change "of" to --or--.

Signed and Sealed this

Sixth Day of October, 1992

*Attest:*

DOUGLAS B. COMER

*Attesting Officer*  *Acting Commissioner of Patents and Trademarks*